(12) United States Patent
Ellis et al.

(10) Patent No.: US 6,509,011 B1
(45) Date of Patent: Jan. 21, 2003

(54) METHOD OF HAIR TREATMENT USING ORGANIC AMINO COMPOUNDS

(75) Inventors: Frances Ann Ellis, Bebington (GB); Matthew Leslie Pearce, Bebington (GB); Cheryl Anne Taylor, Bebington (GB)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 0 days.

(21) Appl. No.: 09/621,291

(22) Filed: Jul. 20, 2000

(30) Foreign Application Priority Data

Jul. 23, 1999 (GB) ............................................... 9917452

(51) Int. Cl.[7] .......................... A61K 7/06; A61K 7/11; A61K 6/00; A61K 7/00; A61K 7/075

(52) U.S. Cl. ................... 424/70.14; 424/401; 424/70.1; 510/119

(58) Field of Search ............................... 424/401, 70.1, 424/70.14; 510/119

(56) References Cited

U.S. PATENT DOCUMENTS

| 3,960,782 A |   | 6/1976  | Daley et al. |
|---|---|---|---|
| 3,997,659 A |   | 12/1976 | Knohl et al. |
| 4,009,256 A |   | 2/1977  | Nowak, Jr. et al. |
| 6,013,250 A | * | 1/2000  | Cannell et al. |

FOREIGN PATENT DOCUMENTS

| DE | 198 16 072 | 10/1999 |
|---|---|---|
| EP | 0498119 | 8/1992 |
| EP | 0567326 | 10/1993 |
| EP | 0890355 | 1/1999 |
| EP | 0978272 | 2/2000 |
| FR | 1293385 A | 12/1962 |
| JP | 53 130442 | 11/1978 |
| JP | 06172140 | 6/1994 |
| JP | 9124434 | 5/1997 |
| JP | 11180837 | 7/1999 |
| WO | 91/10421 | 7/1991 |
| WO | 94/09750 | 5/1994 |
| WO | 95/22311 | 8/1995 |
| WO | 98/51265 | 11/1998 |

OTHER PUBLICATIONS

International Search Report Application No. PCT/GB 00/02456 mailed Oct. 27, 2000.

* cited by examiner

*Primary Examiner*—Thurman K. Page
*Assistant Examiner*—Humera N. Sheikh
(74) *Attorney, Agent, or Firm*—Matthew Boxer

(57) ABSTRACT

A method for reducing hair fiber cuticle loss from hair treated with an oxidative composition, such as an hair bleach, the method comprising the step of contacting the hair, either prior to or after treatment of the hair with the oxidative composition, with a cuticle protective composition comprising an organic amino compound selected from:

(i) basic amino acids;
(ii) urea;
(iii) guanidine;
(iv) salts and/or derivatives of any of (i) to (iii);
(v) mixtures of any of (i) to (iv).

5 Claims, No Drawings

METHOD OF HAIR TREATMENT USING ORGANIC AMINO COMPOUNDS

FIELD OF THE INVENTION

This invention relates to a method of reducing hair fibre cuticle loss from hair treated with an oxidative composition, such as a hair bleach, using certain selected organic amino compounds.

BACKGROUND OF THE INVENTION

Hydrogen peroxide is the most commonly used hair bleaching agent. However, hydrogen peroxide treatment of the hair not only solubilises the melanin but can also lead to undesirable hair qualities, which are in part due to the preferred conditions of conventional peroxide treatment which requires high pH (greater than 9), extended exposure (from 20 to 90 minutes) and relatively high concentration of bleaching solutions (up to 30% volume of oxygen) in order to deliver effective results.

A particular problem associated with hydrogen peroxide treatment of the hair is loss of the hair fibre cuticle, which leads to structural weakness of the hair fibre, and which is exacerbated by subsequent washing and mechanical treatment such as brushing and styling.

We have now found that certain selected organic amino compounds, in particular arginine and urea, are effective for reducing hair fibre cuticle loss from hair previously or subsequently treated with an oxidising agent such as an hair bleach.

U.S. Pat. No. 3,997,659 describes hair bleaching compositions comprising arginine or a protein or polypeptide having a high arginine content, and theorises that the high arginine content of the compositions enhances the penetration of the peroxide into the hair shaft, thereby increasing the rate of melanin bleaching.

In the above case the arginine or proteins are an integral component of the bleaching composition itself. In contrast, the present invention provides a method in which the selected organic amino compounds are incorporated into a conventional hair treatment composition such as a shampoo or conditioner to be applied in a separate stage to the oxidative composition. Advantageously, such a shampoo or conditioner can be applied repeatedly to give a beneficial progressive build-up of the cuticle protection effect, independently of the oxidative composition, for which repeated use would be damaging to the hair.

SUMMARY OF THE INVENTION

The present invention provides a method for reducing hair fibre cuticle loss from hair treated with an oxidative composition, such as an hair bleach, the method comprising the step of contacting the hair, either prior to or after treatment of the hair with the oxidative composition, with a cuticle protective composition comprising an organic amino compound selected from:

(i) basic amino acids;
(ii) urea;
(iii) guanidine;
(iv) salts and/or derivatives of any of (i) to (iii);
(v) mixtures of any of (i) to (iv).

DETAILED DESCRIPTION OF THE INVENTION

According to the method of the present invention, hair is contacted with a cuticle protective composition comprising certain selected organic amino compounds as described above, either prior to, or after treatment of the hair with an oxidative composition.

Preferably the cuticle protective composition is applied after treatment of the hair with the oxidative composition.

Oxidative Composition

By "treatment with an oxidative composition" is meant contacting the hair with an oxidative composition such as an hair bleach.

The composition employed may be formed separately from the hair and then applied. It may also be formed by mixing the separate reactants as they are applied to the hair, for example by mixing the streams from separate aerosol containers as the streams are applied to the hair. It may also be formed by contacting the reactants with the hair to be treated as the reactants are applied to the hair, either concurrently or successively.

Hair bleaching is a chemical process by which the melanin pigment granules are gradually destroyed by the hair bleach resulting in lighter hair colour. Examples of typical hair bleaches include liquid- or creme-based compositions utilizing alkaline hydrogen peroxide solutions as the main oxygen-generating agent to oxidize and bleach the melanin, often in conjunction with a hair colouring process. Just before use, the peroxide is mixed with an alkalizing agent such as ammonia, and the resulting liquid or creme is applied to hair, generally for about 30 to 60 minutes. Further examples of hair bleaches which are typically used include powder compositions based on persulfate salts (ammonium, potassium, sodium) as auxiliary or booster supplies of active oxygen, and silicate and/or carbonate salts as sources of alkalinity. Again, just before use, they are mixed with hydrogen peroxide solutions to form a workable creme that can be applied to the hair. Some powder bleaches even have the hydrogen peroxide itself incorporated in a solid form such as urea peroxide.

Cuticle Protective Composition

The cuticle protective composition comprises an organic amino compound selected from:

(i) basic amino acids;
(ii) urea;
(iii) guanidine;
(iv) salts and/or derivatives of any of (i) to (iii);
(v) mixtures of any of (i) to (iv).

Basic Amino Acids

Basic amino acids (i) may be selected from lysine, arginine and histidine and mixtures thereof. These amino acids are hydrophilic due to their polar side chains. Lysine and arginine are positively charged at neutral pH, whereas histidine can be uncharged or positively charged depending on its local environment.

Arginine is the most preferred amino acid (i) in the method according to the invention.

Alternatively, proteins, polypeptides or other natural extracts having a high basic amino acid content can be used. For example, proteins having a major proportion of arginine units (in the range from about 50 to about 90%, by weight, of the total protein) in their structures are members of that class of proteins known as protamines. The protamine proteins are characterised by having: (a) a low molecular weight, in the range of about 5,000; (b) a high isoelectric point, in the pH range of about 10 to 12; and (c) a high arginine content, in the range from about 50 to about 90%, by weight of the total protein. Suitable examples are described in U.S. Pat. No. 3,997,659.

Proteins of high basic amino acid content as described above can be subjected to acid or base hydrolysis to yield polypeptides which also have a high basic amino acid content. Examples of suitable polypeptides are also described in U.S. Pat. No. 3,997,659, being protamine-derived polypeptides having a molecular weight below about 5,000, a basic pH (10–12), and an arginine content of about 50%, or greater, by weight of the total polypeptide.

Not only may naturally occurring proteins be used, but also synthetic proteins, for example, polylysine and polyarginine, or mixtures thereof.

An example of a suitable natural extract which is rich in arginine is aloe vera extract.

The basic amino acids and the proteins and polypeptides having a basic amino acid content of 50%, or greater, are often isolated from natural sources in the form of salts and hydrosalts, which are also suitable for use according to the invention. Such salts and hydrosalts are formed by reaction with mineral acids such as hydrochloric acid, phosphoric acid, carbonic acid, sulfuric acid, nitric acid, and the like, or the organic acids such as formic acid, acetic acid, lauric acid, chloroacetic acid and the like. A suitable example is arginine hydrochloride.

Guanidine (iii) may also be present as a salts or hydrosalts formed by reaction with mineral or organic acids as described above. A suitable example is guanidine hydrochloride.

The most preferred organic amino compounds in the method according to the invention are arginine and urea and their respective salts and/or hydrosalts.

Mixtures of any of the above organic amino compounds may also be used.

The total amount of organic amino compound may suitably range from 0.01% to 10% by weight based on total weight of the hair treatment composition in which it is employed. Preferably, the amount of organic amino compound ranges from 0.02 to 5% by weight based on total weight, and will ideally range from 0.05% to 2% by weight based on total weight.

Product Form

Cuticle protective compositions according to the invention may suitably take the form of shampoos, conditioners, sprays, mousses, gels, cremes or lotions. Preferred forms are shampoos and conditioners.

Advantageously, the cuticle protective composition comprising an organic amino compound for use in the method according to the invention can be formulated as a shampoo and will then accordingly comprise one or more cleansing surfactants which are cosmetically acceptable and suitable for topical application to the hair.

Suitable cleansing surfactants, which may be used singularly or in combination, are selected from anionic, amphoteric and zwitterionic surfactants, and mixtures thereof.

Examples of anionic surfactants are the alkyl sulphates, alkyl ether sulphates, alkaryl sulphonates, alkanoyl isethionates, alkyl succinates, alkyl sulphosuccinates, N-alkyl sarcosinates, alkyl phosphates, alkyl ether phosphates, alkyl ether carboxylates, and alpha-olefin sulphonates, especially their sodium, magnesium, ammonium and mono-, di-and triethanolamine salts. The alkyl and acyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule.

Preferred anionic surfactants include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauryl isethionate and sodium N-lauryl sarcosinate. The most preferred anionic surfactants are sodium lauryl sulphate, triethanolamine monolauryl phosphate, sodium lauryl ether sulphate 1 EO, 2EO and 3EO, ammonium lauryl sulphate and ammonium lauryl ether sulphate 1EO, 2EO and 3EO.

Examples of amphoteric and zwitterionic surfactants include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates, alkyl amidopropyl hydroxysultaines, acyl taurates and acyl glutamates, wherein the alkyl and acyl groups have from 8 to 19 carbon atoms. Preferred amphoteric and zwitterionic surfactants include lauryl amine oxide, cocodimethyl sulphopropyl betaine and preferably lauryl betaine, cocamidopropyl betaine and sodium cocamphopropionate.

The cleansing surfactant(s) may be present in shampoo compositions for use according to the invention in a total amount of from about 1 to about 40% by weight based on the total weight of the shampoo composition, preferably from about 2 to about 30% by weight, optimally from about 10% to 30% by weight.

Shampoos for use according to the invention can also include nonionic surfactants to help impart aesthetic, physical or cleansing properties to the composition. The nonionic surfactant can be included in an amount ranging from 0% to about 5% by weight based on total weight.

For example, representative nonionic surfactants include condensation products of aliphatic ($C_8$–$C_{18}$) primary or secondary linear or branched chain alcohols or phenols with alkylene oxides, usually ethylene oxide and generally having from 6 to 30 ethylene oxide groups.

Other representative nonionics include mono- or di-alkyl alkanolamides. Examples include coco mono- or di-ethanolamide and coco mono-isopropanolamide.

Further nonionic surfactants which can be included are the alkylpolyglycosides (APGs). Typically, the APG is one which comprises an alkyl group connected (optionally via a bridging group) to a block of one or more glycosyl groups. Preferred APGs are defined by the following formula:

wherein R is a branched or straight chain alkyl group which may be saturated or unsaturated and G is a saccharide group.

R may suitably represent a mean alkyl chain length of from about $C_5$ to about $C_{20}$. Preferably R represents a mean alkyl chain length of from about $C_8$ to about $C_{12}$. Most preferably the value of R lies between about 9.5 and about 10.5. G may be selected from $C_5$ or $C_6$ monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more. Preferably, the value of n lies in the range of from about 1.1 to about 2. Most preferably the value of n lies in the range of from about 1.3 to about 1.5.

Suitable alkyl polyglycosides are commercially available and include for example those materials identified as: Oramix NS10 ex Seppic; Plantaren 1200 and Plantaren 2000 ex Henkel. Likewise shampoos for use according to the invention can include other emulsifiers, conditioning agents, inorganic salts, humectants and similar materials to provide the composition with desirable aesthetic or physical properties.

Representative conditioning agents include silicones. Silicones are particularly preferred conditioning agents for hair.

Representative silicones include volatile and non-volatile silicones, such as for example polyalkylsiloxanes (optionally end-capped with one or more hydroxyl groups), polyalkylaryl siloxanes, siloxane gums and resins, cyclomethicones, aminofunctional silicones, quaternary silicones and mixtures thereof.

Preferred silicones include polydimethylsiloxanes (of CTFA designation dimethicone), siloxane gums, aminofunctional silicones (of CTFA designation amodimethicone) and hydroxylated polydimethylsiloxanes (of CTFA designation dimethiconol).

Various methods of making emulsions of particles of silicones are available and are well known and documented in the art.

Suitable silicone emulsions are commercially available in a pre-emulsified form. This is particularly preferred since the pre-formed emulsion can be incorporated into the shampoo composition by simple mixing.

Examples of suitable pre-formed emulsions include emulsions DC2-1310, DC2-1865, DC2-1870, DC2-1766 and DC2-1784, available from Dow Corning. These are emulsions of dimethiconol. Siloxane gums are also available in a pre-emulsified form, which is advantageous for ease of formulation. A preferred example is the material available from Dow Corning as DC X2-1787, which is an emulsion of cross-linked dimethiconol gum.

The amount of silicone incorporated into compositions for use according to the invention depends on the level of conditioning desired and the material used. A preferred amount is from 0.01 to about 10% by weight of the total composition although these limits are not absolute. The lower limit is determined by the minimum level to achieve conditioning and the upper limit by the maximum level to avoid making the hair and/or skin unacceptably greasy. We have found that an amount of silicone of from 0.5 to 1.5% by weight of the total composition, is a particularly suitable level.

A further preferred class of conditioning agents are per-alk(en)yl hydrocarbon materials, used to enhance the body, volume and stylability of hair.

EP 567 326 and EP 498 119 describe suitable peralk(en)yl hydrocarbon materials for imparting stylability and enhanced body to hair. Preferred materials are polyisobutylene materials available from Presperse, Inc. under the PERMETHYL trade name.

The amount of per-alk(en)yl hydrocarbon material incorporated into compositions for use according to the invention depends on the level of body and volume enhancement desired and the specific material used. A preferred amount is from 0.01 to about 10% by weight of the total composition although these limits are not absolute. The lower limit is determined by the minimum level to achieve the body and volume enhancing effect and the upper limit by the maximum level to avoid making the hair unacceptably stiff. We have found that an amount of per-alk(en)yl hydrocarbon material of from 0.5 to 2% by weight of the total composition is a particularly suitable level.

Shampoo compositions for use according to the invention may also include a polymeric cationic conditioning compound that is substantive to the hair and imparts conditioning properties to the hair.

The polymeric cationic conditioning compound will generally be present at levels of from 0.01 to 5%, preferably from about 0.05 to 1%, more preferably from about 0.08% to about 0.5% by weight. Synthetic or naturally derived polymers having a quaternised nitrogen atom are useful. The molecular weight of the polymer will generally be between 5,000 and 10,000,000, typically at least 10,000 and preferably in the range 100,000 to about 2,000,000.

Representative synthetic quaternised polymers include, for example: cationic copolymers of 1-vinyl-2-pyrrolidine and 1-vinyl-3-methyl-imidazolium salt (e.g., Chloride salt) (referred to in the industry by the Cosmetic, Toiletry, and Fragrance Association, "CTFA". as Polyquaternium-16); copolymers of 1-vinyl-2-pyrrolidine and dimethylaminoethyl methacrylate (referred to in the industry by CTFA as Polyquaternium-11); cationic diallyl quaternary ammonium-containing polymers including, for example, dimethyldiallylammonium chloride homopolymer (referred to in the industry (CTFA) as Polyquaternium 6); mineral acid salts of amino-alkyl esters of homo-and co-polymers of unsaturated carboxylic acids having from 3 to 5 carbon atoms, as described in U.S. Pat. No. 4,009,256; and cationic polyacrylamides as described in WO95/22311.

Representative naturally-derived quaternised polymers include quaternised cellulosic compounds and cationic guar gum derivatives, such as guar hydroxypropyltrimonium chloride. Examples are JAGUAR C-13S, JAGUAR C-15, and JAGUAR-C17, commercially available from Meyhall in their JAGUAR trademark series.

Compositions for use in accordance with the invention may also be formulated as a hair conditioner for the treatment of hair (typically after shampooing) and subsequent rinsing. Such formulations will then accordingly comprise one or more conditioning surfactants which are cosmetically acceptable and suitable for topical application to the hair.

Suitable conditioning surfactants are selected from cationic surfactants, used singly or in admixture. Examples include quaternary ammonium hydroxides or salts thereof, e.g chlorides.

Suitable cationic surfactants include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, and the corresponding hydroxides thereof. Further suitable cationic surfactants include those materials having the CTFA designations Quaternium-5, Quaternium-31 and Quaternium-18. Mixtures of any of the foregoing materials may also be suitable. A particularly useful cationic surfactant for use in hair conditioners of the invention is cetyltrimethylammonium chloride, available commercially, for example as GENAMIN CTAC, ex Hoechst Celanese. In hair conditioners for use according to the invention, the level of cationic surfactant is preferably from 0.01 to 10%, more preferably 0.05 to 5%, most preferably 0.1 to 2% by weight of the composition.

Conditioners for use according to the invention advantageously incorporate a fatty alcohol material. The combined use of fatty alcohol materials and cationic surfactants in conditioning compositions is believed to be especially advantageous, because this leads to the formation of a lamellar phase, in which the cationic surfactant is dispersed.

Representative fatty alcohols comprise from 8 to 22 carbon atoms, more preferably 16 to 20. Examples of suitable fatty alcohols include cetyl alcohol, stearyl alcohol and mixtures thereof.

The level of fatty alcohol materials is conveniently from 0.01 to 10%, preferably from 0.1 to 5% by weight of the composition. The weight ratio of cationic surfactant to fatty alcohol is suitably from 10:1 to 1:10, preferably from 4:1 to 1:8, optimally from 1:1 to 1:4.

Conditioners for use according to the invention can include other emulsifiers, conditioning agents, inorganic salts, humectants and similar materials to provide the composition with desirable aesthetic or physical properties. Silicones, as described above for shampoo compositions, are particularly preferred conditioning agents for hair.

As further optional components for inclusion in shampoo or conditioner compositions for use according to the invention, in addition to water, may be mentioned the following conventional adjunct materials known for use in cosmetic compositions: suspending agents, thickeners, pearlescing agents, opacifiers, salts, perfumes, buffering agents, colouring agents, emollients, moisturisers, foam stabilisers, sunscreen materials, antimicrobial agents, preservatives, antioxidants, natural oils and extracts, propellants.

The invention will now be further illustrated by the following, non-limiting Example.

EXAMPLE

Cuticle abrasion and sensory experiments were performed on bleached hair with unbleached "virgin" hair as a control.

A shampoo base was used to treat hair switches:

| | |
|---|---|
| Sodium lauryl ether sulphate (2EO) | 12% |
| Cocamidopropyl betaine | 2% |
| Water | to 100% |

Two samples of the above formulation were prepared, with the addition of 0.2% arginine to one of the samples.

Four sets of switches were used and treated as follows:

Set 1. Bleached switches washed 6 times in base, with final base wash containing 0.2% arginine.

Set 2. Bleached switches based washed 6 times in base with 0.2% arginine

Set 3. Bleached switches washed 6 times in base without 0.2% arginine

Set 4. Unbleached virgin hair washed in base without arginine.

The treated samples were subjected to cuticle abrasion (in duplicate).

Results

There was significantly more cuticle removed from the sample that had not received the arginine treatment (set 3). When examined, this cuticle sample was clumped together in sheets and cortex material was clearly evident.

The sample that had received arginine treatment throughout the washes (set 2) had significantly better cuticle cohesion. The cuticle was closer in sample size and appearance to the unbleached sample.

The sample that was treated with arginine at the final wash only (set 1) showed evidence of improved cuticle cohesion. Significantly less cuticle was removed than set 3. It was closer in sample size and appearance to set 2.

What is claimed is:

1. A method for reducing hair fibre cuticle loss from hair treated with an oxidative, such as a hair bleach, the method comprising the step of contacting the hair, either prior to or after treatment of the hair with the oxidative composition, with a cuticle protective composition comprising at least one organic amino compound wherein said at least one organic amino compound is selected from the group consisting of:

(i) a basic amino acid selected from the group consisting of lysine, arginine, histidine, and mixtures thereof;

(ii) urea;

(iii) guanidine;

(iv) salts and/or derivatives of any of (i) to (iii); and (v) mixtures of any of (i) to (iv).

2. A method according to claim 1, in which the organic compound is selected from the group consisting of arginine, urea and mixtures thereof.

3. A method according to claim 1, in which the amount of organic amino compound ranges from 0.01% to 10% by weight based on total weight.

4. A method according to claim 1, in which the cuticle protective composition is formulated as a shampoo composition.

5. A method according to claim 1, in which the cuticle protective composition is formulated as a hair conditioner.

* * * * *